United States Patent [19]

Wolf et al.

[11] Patent Number: 4,979,942

[45] Date of Patent: Dec. 25, 1990

[54] TWO COMPONENT SYRINGE DELIVERY SYSTEM

[75] Inventors: Stephen J. Wolf, Hillsborough; Robert K. Mart, Martinsville, both of N.J.; Scott C. Otto, Yardley, Pa.

[73] Assignee: Johnson & Johnson Medical, Inc., Arlington, Tex.

[21] Appl. No.: 422,259

[22] Filed: Oct. 16, 1989

[51] Int. Cl.[5] ............................................. A61M 37/00
[52] U.S. Cl. .................................... 604/83; 604/191; 222/137; 222/145
[58] Field of Search ...................... 604/72, 82, 83, 173, 604/191, 232, 266, 269; 222/129, 137, 145, 327

[56] References Cited

U.S. PATENT DOCUMENTS

| | | | |
|---|---|---|---|
| 808,635 | 1/1906 | Ciolfi et al. | 604/8 |
| 1,837,932 | 12/1931 | Weigle | 604/82 X |
| 2,112,160 | 3/1938 | Johnson | 128/234 |
| 3,223,083 | 12/1965 | Cobey | 128/92 |
| 3,467,096 | 9/1969 | Horn | 128/218 |
| 3,749,084 | 7/1973 | Cucchiara | 604/191 X |
| 3,767,085 | 10/1973 | Cannon et al. | 222/137 X |
| 3,828,980 | 8/1974 | Creighton et al. | 222/137 |
| 3,875,939 | 4/1975 | Bolduc et al. | 604/82 X |
| 3,955,930 | 5/1976 | Shapiro | 222/137 X |
| 4,040,420 | 8/1977 | Speer | 128/218 |
| 4,044,757 | 8/1977 | McWhorter et al. | 604/82 X |
| 4,069,814 | 1/1978 | Clemens | 604/83 X |
| 4,109,653 | 8/1978 | Kozam et al. | 128/218 |
| 4,260,077 | 4/1981 | Schroeder | 222/137 |
| 4,359,049 | 11/1982 | Redl et al. | 128/218 |
| 4,381,778 | 5/1983 | Kozam et al. | 604/191 |
| 4,512,768 | 4/1985 | Rangaswamy | 604/191 |
| 4,522,622 | 6/1985 | Peery et al. | 604/191 |
| 4,609,371 | 9/1986 | Pizzino | 604/191 |
| 4,610,666 | 9/1986 | Pizzino | 604/191 |
| 4,631,055 | 12/1986 | Redl et al. | 604/82 |
| 4,643,724 | 2/1987 | Jobe | 604/232 |
| 4,679,446 | 7/1987 | Sheenan et al. | 73/864.13 |
| 4,689,042 | 8/1987 | Sarnoff et al. | 604/89 |
| 4,735,616 | 4/1988 | Eibl et al. | 604/191 |
| 4,738,379 | 4/1988 | Takasugi | 222/95 |
| 4,753,536 | 6/1988 | Spehar et al. | 366/339 |
| 4,773,419 | 9/1988 | Tountas | 128/327 |
| 4,846,405 | 7/1989 | Zimmermann | 239/422 |
| 4,874,368 | 10/1989 | Miller et al. | 604/82 |
| 4,902,281 | 2/1990 | Avoy | 604/191 |

Primary Examiner—John D. Yasko
Assistant Examiner—Adam J. Cermak
Attorney, Agent, or Firm—Paul A. Coletti

[57] ABSTRACT

A fluid delivery system where two reactive fluids are delivered simultaneously and separately from a pair of syringes to a delivery site. In one embodiment, a length of tubing exits one syringe and passes through a cannula exiting from the other syringe, to deliver both fluids, separately, but in a controlled volume and space to the delivery site. Alternately, the fluids can mix within the cannula, but its configuration prevents clogging at the delivery site.

14 Claims, 4 Drawing Sheets

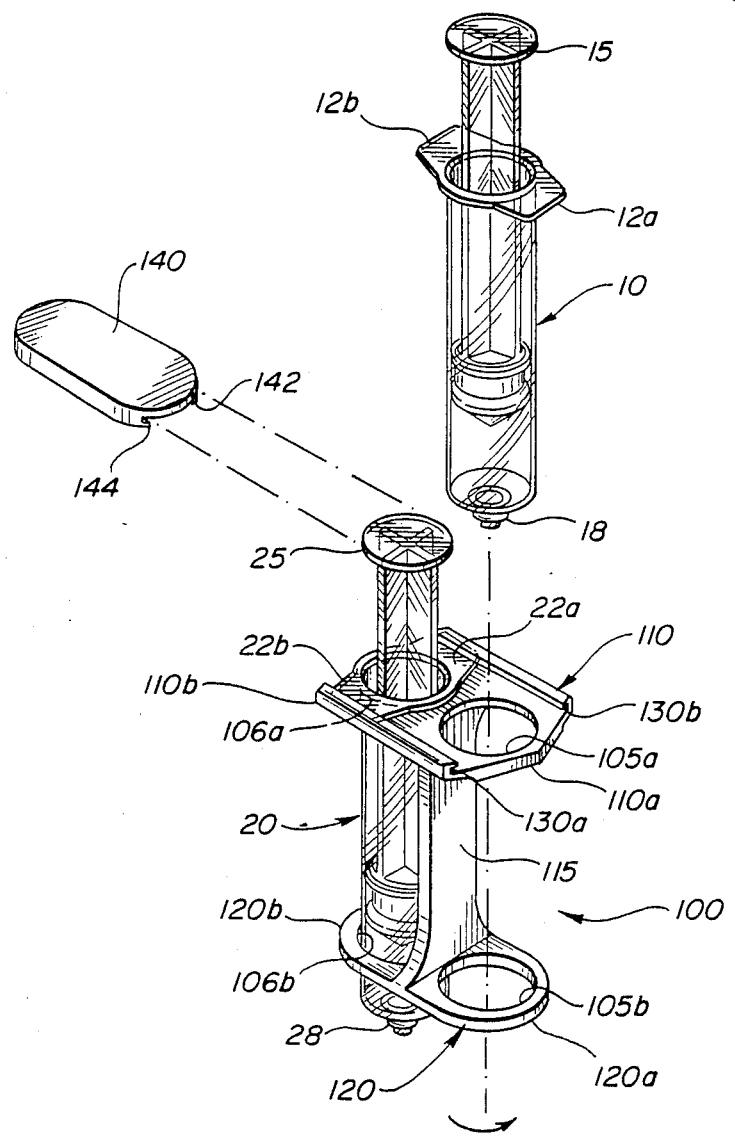

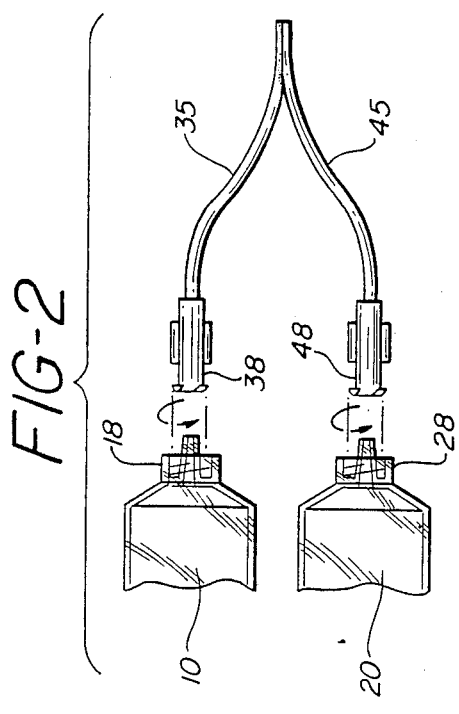
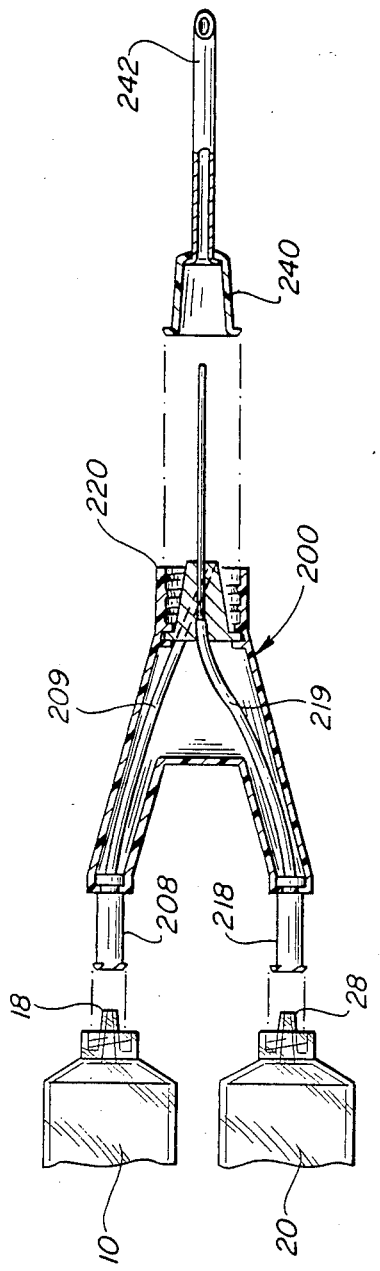

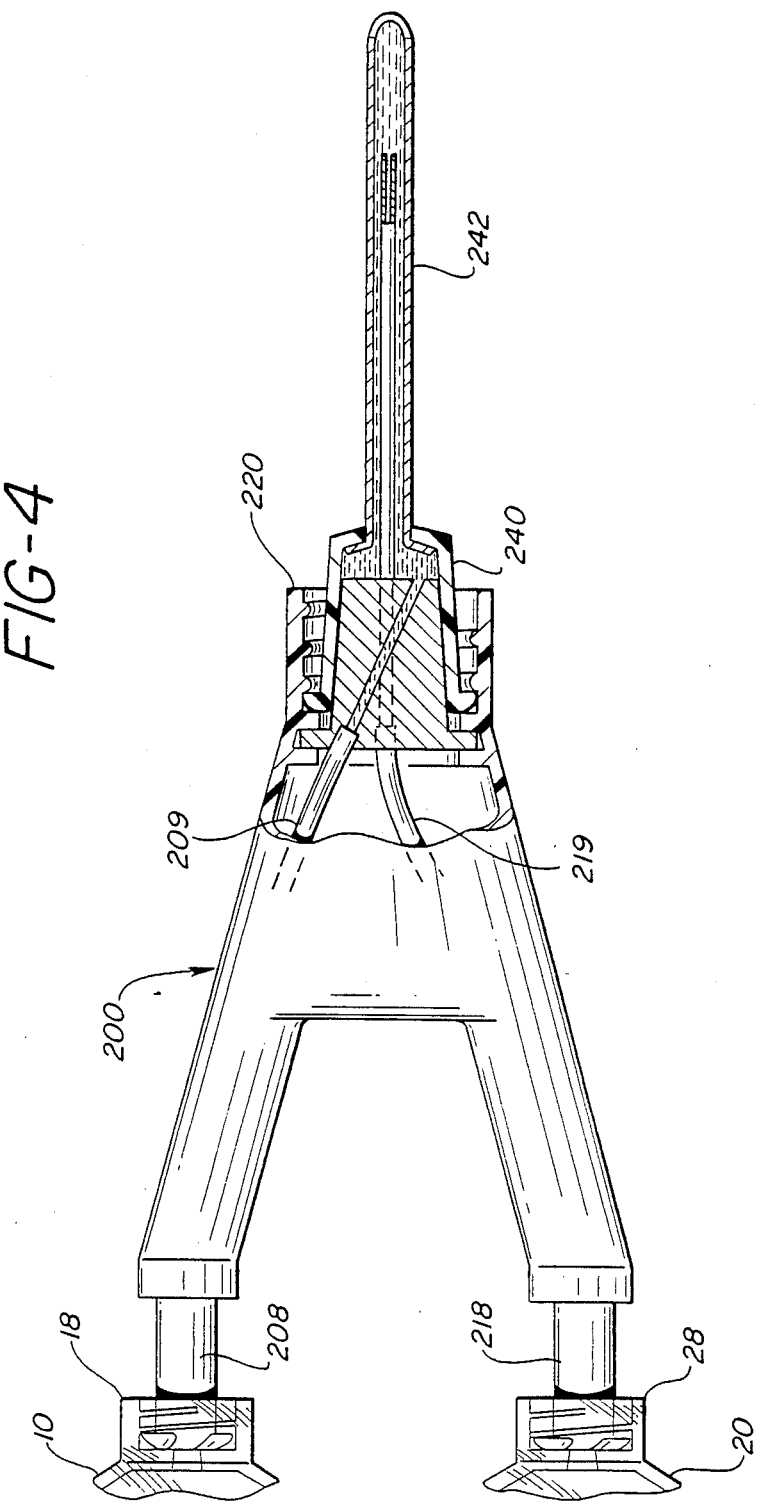

TWO COMPONENT SYRINGE DELIVERY SYSTEM

FIELD OF THE INVENTION

This invention relates to a system for delivery of two separate components. More specifically, this invention relates to a system for delivery of two separate components by syringe, where the components are mixed at the site of delivery. Most specifically, this invention relates to the delivery of two components by syringe where the components are mixed at the site of delivery and the components are delivered along generally equivalent path lengths.

BACKGROUND OF THE INVENTION

In the medical field, it may be desired to deliver two separate components to an active medical site. For instance, in the production of fibrin glue, it is desirable to deliver thrombin and fibrinogen to the same delivery site. As with the case in the formation of fibrin glue, it may be desirable to deliver the two components simultaneously and separately so that they only mix at the delivery site. For instance, with fibrin glue formation, if the components are delivered and mixed within a delivery system and then delivered to the delivery site, it is possible to clog the delivery system due to the adhesive nature of fibrin glue. On the other hand, other systems may need mixing at some point within the delivery tube. Of course, clogging of this tube is undesirable.

Previous attempts at mixing the separate chemicals in a delivery system at the delivery site have met with little success. Therefore, common delivery systems may contain the improper mixture ratio of components, or have components mixed within the delivery system and then delivered, albeit over a short path length, to the delivery site. Devices which have attempted simultaneous delivery have been lacking in mechanisms for proper attachment of the delivery tubes. When these tubes clog, forces may cause the delivery tubes to separate from the syringe. Furthermore, systems where mixture is made at the delivery site are very difficult to manipulate. Frequent clearing of clogged components is necessary. Certainly, these present systems have all been virtually impossible to operate with one hand.

Finally, none of the typical two component delivery systems, regardless of the location of the mixture of the two components, have been capable of operating with typical hypodermic syringes locked in place within a sturdy, lightweight, and functional locking mechanism that ensures simultaneous delivery of both separate components in the delivery system. The two component delivery systems have been either too bulky to deliver the two components adequately, or too flimsy to hold the typical hypodermic syringes. Because these systems operate with one hand, they are hard to formulate within a convenient package.

SUMMARY OF THE INVENTION

Therefore, it is an object of the invention to provide a two component delivery system where the components are delivered at the delivery site simultaneously and separately.

It is further an object of the invention to provide a two component delivery system where the components are delivered separately and simultaneously to the delivery site along a single cannula.

Another object of the invention is to provide a delivery system which prevents clogging of mixed fluids by having the fluids come into contact near the exit port and toward the delivery site.

It is further an object of the invention to provide a two component syringe delivery system where the single cannula of the invention i adaptable for use with two typical hypodermic syringes.

It is yet another object of the invention to provide a two component syringe delivery system where the syringes in the system can be managed and held in place securely by a holder which allows for simultaneous delivery of the two components through equivalent pressures on the two syringes.

It is a final object of the invention to provide a two component syringe delivery system in which clogging is prevented along the entire length of the fluid paths of both components by preventing mixture of the two components until both components have exited the system, so that mixture is obtained at the delivery site.

These and other objects of the invention are accomplished in a system whereby two typical hypodermic syringes can be locked in place within a syringe holder to provide uniform delivery of the two components. The syringe holder is formed such that the syringes are insertable through the holder itself and then locked in place along a channeled upper surface to prevent movement of either syringe. In addition, a plunger clip is inserted over the plungers of the syringes so that pressure can be equally distributed to both syringes during operation of the system.

The locked syringes are then attached via luer lock fittings to a double tubing system. The tubes are attached so that they both reach the delivery site along roughly equivalent path lengths, so that the mixture of the two components can be made at the delivery site.

Alternately, the two components are delivered into an assembled luer attachment which comprises a double luer (or luer lock) fitting attachable to both syringes. Within the syringes, there is described a double fluid path so that the fluids run parallel to each other at the exit of the luer attachment. At the attachment exit, there is insertable a single cannula. Projecting from the attachment is a length of tubing containing one of the elements. This tubing fits within the cannula so that one element travels the length of the cannula without contacting the cannula, down the length of the tubing. The other element exits the attachment and is forced around the tubing through the length of the cannula. The elements mix at or near the exit from the cannula, the first element exiting through the tubing and the second element exiting from the cannula and around the tubing. Again, the elements mix at or near the delivery site, and any reactive material is easily ejected from the large diameter cannula.

The invention described in this summary will be better understood by reference to the attached figures and the detailed description cf the invention.

DETAILED DESCRIPTION OF THE DRAWINGS

The invention is described in connection with the accompanying figures in which:

FIG. 1 is a perspective view of the syringes of the two component delivery system inserted into the syringe holder;

FIG. 2 is a assembly drawing of an embodiment of the present invention in which vinyl tubings are connected at the delivery site;

FIG. 3 is an exploded elevation view in partial cross-section of an alternate embodiment of the present invention incorporating a single cannula fitted over a separate length of tubing at the delivery site;

FIG. 4 is a elevation view in partial cross-section of the assembled tubing/cannula system.

DETAILED DESCRIPTION OF THE INVENTION

Figure 5:
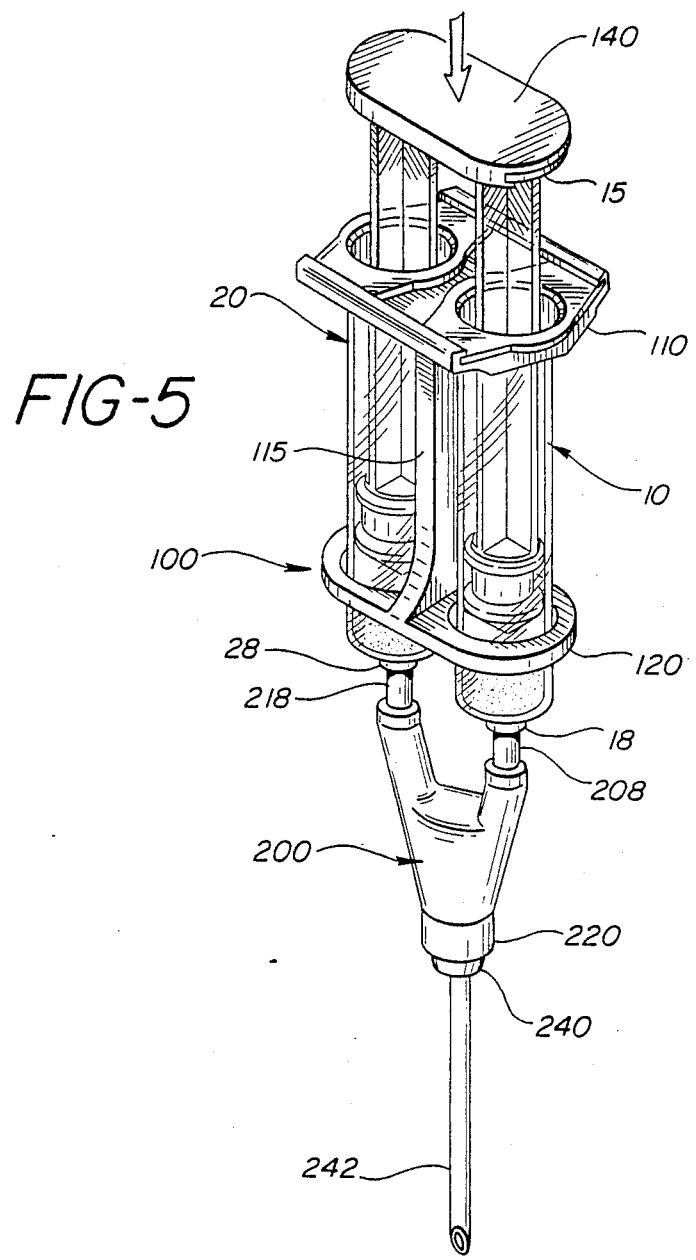
FIG. 5 is an assembled two component delivery system incorporating the invention.

As seen in FIGS. 1-5, the two component syringe delivery system has as its basis two separate syringes 10, 20 for delivery of separate components. For instance, in one syringe there may be fibrinogen, and in an alternate syringe there may be thrombin. The combination will be mixed together at the delivery site for the formation of fibrin glue.

The first component of the delivery system to be discussed is the holding mechanism 100 which assures proper delivery of the two components simultaneously. In the present holder 100, there are located bored holes 105a, 105b and 106a, 106b, for both syringes and two sets of flanges 110, 120 for locking, separated by arm 115. The lower set of flanges 120a, 120b, keep the syringes 10, 20 in place from rotating around the upper set of flanges 110a, 110b. The upper flanges 110a, 110b ensure that the two syringes 10, 20 remain in desired position.

Located in the upper flanges 110a, 110b are channels 130a, 130b which form a locking mechanism for the syringes. On the syringes 10, 20 there are ears 12a, 12b and 22a, 22b, which are usually gripped during individual operation of the syringes. These ears 12a, 12b, 22a, 22b, can be incorporated into channels 130a, 130b by first inserting the syringes 10, 20 into the sets of holes 105, 106 and then rotating the ears of the syringes into channels 130a, 130b, as with locked syringe 20 in FIG. 1.

When locked in place, both syringes 10, 20 are fixed in parallel or at an angle and can be given the appropriate amount of pressure to deliver simultaneously the two components of the system. When angled, the syringes 10, 20 provide uniform mixing of the two components and can be used in a spray which mixes either at or near the delivery site. Simultaneous delivery is accomplished by the placement of plunger clip 140 at the plunger heads 15, 25 of the two syringes 10, 20. It is to be noticed that the clip 140 itself has channeled grooves 142, 144 which fit along the outer diameters of the heads 15, 25 of the two syringes 10, 20, so that the heads 15, 25 are positioned at the desired angle along the entire fluid paths. Heads 15, 25 are able to move within the clip 140 so that depression of both syringes 10, 20 is accomplished simultaneously.

Thus, the user grasps the syringes with the thumb crossing the length of cap 140, the palm bridging the length of syringes 10, 20 and the index and third finger holding the holder 100 across the flanges 110a, 110b. By forcing the thumb on the cap 140, equivalent pressures are provided to both syringes 10, 20, and equivalent amounts of fluid are delivered from both syringes 10, 20.

As further seen in FIG. 2, exiting syringes 10, 20 there are luer lock fittings 38, 48 which can be attached to the luer lock hubs 18, 28 of both syringes 10, 20. These luer lock fittings 38, 48 are attached at their opposite ends to flexible vinyl tubing 35, 45 forming a double cannula. Flexible tubing allows rotation of the luer lock fittings 38, 48 This double cannula is joined so that the dual cannula tubings 35, 45 are attached at the ends, usually with solvent adhesive. Thus, when the equivalent amounts of pressure are provided, the dual cannula 35, 45 is able to deliver the same amount of fluid from each syringe 10, 20. These cannulas will generally have outer diameters of about 0.060" and inner diameters of about 0.020", with lengths anywhere from 1" to 5". Because the tubings 35, 45 are cut off at equivalent lengths, there is simultaneous delivery of fluid from both syringes.

Alternately, a single cannula solution is found in FIGS. 3-5. There is shown connector 200 which has a double luer fitting 208, 218. This fitting 208, 218 may be a general or luer lock fitting. This connector 200 contains hollowed double fluid path 209, 219 which is formed from tubing or plastic molding. At the end of the double fluid path 209, 219 there is luer hub 220. Attached through luer hub 220 is fluid path 219, which allows the fluid from syringe 20 to flow directly through the hub 220. Fluid in first path 209 is deposited into hub 220. Thus, the central portion of hub 220 can be filled with fluid from syringe 10.

Single cannula fitting 240 has a cannula 242 extending from it so that cannula 242 would allow approximately twice the volume of fluid as compared to fluid path 219. When single cannula 240 is fit within the luer hub 220, therefore, equivalent volumes of the fluid from syringe 10 travel the length of the cannula 242 half filled with fluid path 219, with equivalent volumes of the fluid from syringe 20 flowing through the fluid path 219. Again, equivalent volumes of both fluids reach the end of the cannula 242 simultaneously Mixing can take place outside the cannula 242 sr that clogging is prevented along the cannula 242.

In addition, fluid path 219 may end at some point near the end of cannula 242, so that mixing occurs just before the delivery site. Reacted materials are easily ejected from cannula 242 since its diameter is larger than either of paths 209, 219.

Thus, with the two component delivery system, equivalent pressures are derived and these equivalent pressures are able to provide for equivalent amounts of fluid flowing the length cf the system. When the equivalent amounts of fluid are ejected from the system, they are able to mix at the delivery site so that clogging is prevented in the system. In addition, chemical reactions can take place outside the cannula, or pre-mix before delivery without clogging as desired. Finally, the entire system is able to Provide the proper amounts of fluid directly to the delivery site.

These and other objects of the present invention are to be determined from the attached claims and their equivalents.

What is claimed is:

1. A system for simultaneous delivery of fluids from two syringes comprising: an attachment containing a pair of luer-type connectors for luer connection to each of said syringes, each said luer connection having attached to it a fluid path, one said path exiting from said attachment at a luer hub, the other said path exiting from said attachment in a length of tubing; and a single cannula for luer attachment to said luer hub, said tubing fitting within said cannula.

2. The system of claim 1 wherein said cannula has twice the cross-sectional area of said tubing so that said single cannula with said tubing fit within said cannula, and said tubing, deliver generally equivalent volumes of fluid from each of said different syringes.

3. The system of claim 1 further containing a holder having two sets of flanges, each said flange having first and second holes described therein, said first hole in the first said flange aligned with said first hole in the said second flange and said second hole in said first flange aligned with said second hole in said second flange and each said first and second holes large enough to fit a syringe therein, such that when each said syringe is emplaced within a first and second holes of each flange, said syringes are parallel.

4. The system of claim 3 further containing a plurality of ears on said syringes, said syringes held in place by a pair of channeled grooves on one of said flanges, said grooves locking the ears of said syringes within said grooves when said syringes are rotated within said groove.

5. The system of claim 4 wherein said cannula has twice the cross-sectional area of said tubing so that said system delivers equivalent volumes of each fluid at the end of said cannula.

6. The system of claim 5 wherein a plunger clip with a pair of channeled grooves is emplaceable on the plungers of said syringes such that said channeled grooves hold said plungers, and pressing said clip causes the delivery of each said fluid from each said syringe.

7. For use with two syringes, each said syringe having a diameter, a pair of ears and a plunger for firing said syringe, a holder for locking said syringes together, said holder comprising a pair of flanges separated by an arm, each said flange having a pair of holes, one hole on each said flange corresponding to one syringe diameter and one hole on each said flange corresponding to the opposite syringe diameter, each said corresponding hole on each flange aligned on one side of said arm, such that when said syringes are passed through said holes such that each said syringe is aligned with one of said pair of holes, said syringes are fixed relative to one another, and further comprising an attachment containing a pair of luer-type connectors for luer connection to each of said syringes, each said luer connection having attached to it a fluid path, one said path exiting from said attachment at a luer hub, the other said path exiting from said attachment in a length of tubing; and a single cannula for luer attachment to said luer hub, said tubing fitting within said cannula.

8. The holder of claim 7 wherein a plunger clip with a pair of channeled grooves is emplaceable on the plungers of said syringes such that said channeled grooves hold said plungers, and pressing said clip causes the delivery of each said fluid from each said syringe.

9. The holder of claim 8 wherein each syringe is connected to a separate tube such that fluid exits from each tube occurs simultaneously at a single delivery site.

10. A system for simultaneous delivery of fluids from two syringes comprising a pair of syringes, each said syringe connected to a connector containing a length of tubing exiting one said syringe and a cannula exiting the second said syringe, said tubing fitting within said cannula, and wherein said cannula has twice the cross-sectional area of said tubing so that cannula with said tubing fit within said cannula, and said tubing, delivery generally equivalent volumes of fluid from each of said different syringes.

11. The system of claim 10 wherein said cannula with said tubing emplaced therein, and said tubing, deliver equivalent volumes of fluid from each said syringe to a delivery site.

12. The system of claim 11 further containing a holder having two parallel sets of flanges, each said flange having first and second holes described therein, said first hole in the first said flange aligned with said first hole in the said second flange and said second hole in said first flange aligned with said second hole in said second flange and each said first and second holes large enough to fit a syringe therein, such that when each said syringe is emplaced within a first and second holes of each flange, said syringes are parallel.

13. The system of claim 12 wherein said syringe contain a plurality of ears and are held in place by a pair of channeled grooves on one of said flanges, said grooves locking the ears of said syringes within said grooves when said syringes are rotated within said grooves.

14. The system of claim 13 wherein a plunger clip with a pair of channeled grooves is emplaceable on the plungers of said syringes such that said channeled grooves hold said plungers, and pressing said clip causes the delivery of each said fluid from each said syringe.

* * * * *